United States Patent

Elbe

[11] Patent Number: 4,739,118
[45] Date of Patent: Apr. 19, 1988

[54] PROCESS FOR THE PREPARATION OF HYDROXYBENZALDOXIME O-ETHERS

[75] Inventor: Hans-Ludwig Elbe, Wuppertal, Fed. Rep. of Germany

[73] Assignee: Bayer Aktiengesellschaft, Leverkusen, Fed. Rep. of Germany

[21] Appl. No.: 907,209

[22] Filed: Sep. 12, 1986

[30] Foreign Application Priority Data

Sep. 28, 1985 [DE] Fed. Rep. of Germany ....... 3534731

[51] Int. Cl.$^4$ ............................................. C07C 131/00
[52] U.S. Cl. .................................................. 564/256
[58] Field of Search ......................................... 564/256

[56] References Cited

U.S. PATENT DOCUMENTS 3,124,613  3/1964  Wehrmeister ..................... 564/266

FOREIGN PATENT DOCUMENTS 870787  6/1961  United Kingdom .

Primary Examiner—Donald B. Moyer
Assistant Examiner—L. Hendriksen
Attorney, Agent, or Firm—Sprung Horn Kramer & Woods

[57] ABSTRACT

A process for the preparation of a hydroxybenzaldoxime O-ether of the formula

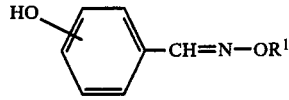

in which
$R^1$ is alkyl, alkenyl or alkynyl
comprising reacting a hydroxybenzaldehyde of the formula

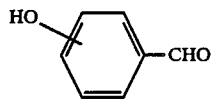

in the presence of an acid catalyst at a temperature between 50° to 150° C. with a ketoxime O-ether of the formula

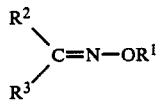

in which
$R^2$ and $R^3$ each independently is an aliphatic cycloaliphatic or aromatic radical, or
$R^2$ and $R^3$, together with the carbon atom to which they are bonded are cycloalkyl.

Advantageously, the hydroxybenzaldehyde is 4-hydroxybenzaldehyde, the acid catalyst is a Lewis acid, the reaction is effected in a diluent at a temperature between 50° and 100° C., 1 to 10 mols of the ketoxime O-ether are present per mol of hydroxybenzaldehyde and the catalyst is present in 0.01 to 10 mol % based on the ketoxime O-ether. The products are intermediates for agricultural and pharmaceutical chemicals.

9 Claims, No Drawings

PROCESS FOR THE PREPARATION OF HYDROXYBENZALDOXIME O-ETHERS

The invention relates to a new process for the preparation of known hydroxybenzaldoxime O-ethers which can be used as intermediates for the synthesis of compounds having fungicidal, insecticidal and antimycotic activity.

It has already been disclosed that certain hydroxybenzaldoxime O-ethers can be prepared by reaction of hydroxybenzaldehydes with the appropriate hydroxylamine derivatives (compare EP-OS (European Published Specification) No. 0,076,370 and EP-OS (European Published Specification) No. 0,115,828). The relevant reaction can be illustrated by the equation below:

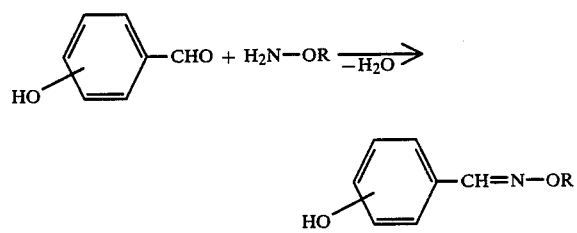

R = alkyl, alkenyl or alkynyl.

However, a disadvantage of this process is that pure hydroxylamine derivatives or their salts are required. These are, however, such costly starting materials that their use for a preparation of hydroxy-benzaldoxime O-ethers on an industrial scale is uninteresting. It is also unfavorable that, normally, the costly hydroxylamine derivative is used in excess in order to achieve as nearly complete reaction of the aldehyde as possible.

Furthermore, it has been disclosed that benzaldoxime O-ethers which do not contain a hydroxyl group in the phenyl moiety can be prepared by reaction of benzaldoxime with alkyl, alkenyl or alkynyl halides in the presence of bases (compare Houben-Weyl, "Methoden der Organischen Chemie" (Methods of Organic Chemistry) volume 10/4, pages 217–223, published by Georg Thieme, Stuttgart, 1971). The relevant reaction can be illustrated by the equation below:

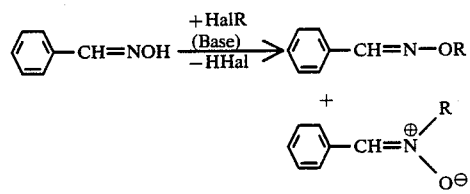

R = alkyl, alkenyl or alkynyl,
Hal = halogen.

This process has the disadvantage that it always results in mixtures of benzaldoxime O-ethers and undesired nitrones. Although it is possible to increase the proportion of oxime ether by employing the benzaldoxime, which is used as starting material, in the form of a salt,—for example in the form of the silver salt, this variant does not represent an industrially acceptable alternative.

The alkylation of syn-benzaldoxime sodium salt with alkyl halides in alcoholic solution provides the O-alkyl ethers in yields of 50 to 80%. However, when using antibenzaldoxime under the same conditions exclusively N-alkylation to give the nitrone takes place (compare J. Org. Chem. 32, 261 (1967)).

Corresponding reactions are also described under phase-transfer conditions (compare Chemistry Letters, 1980, pages 869–870). Thus, the butylation of synbenzaldoxime in a phase-transfer-catalyzed reaction (methylene chloride, aqueous sodium hydroxide solution, tetrabutylammonium bromide) provides the syn-benzaldoxime O-butyl ether in a yield of 58%, whereas where anti-benzaldoxime is used the corresponding nitrone is the main product.

Furthermore, an industrial process for the preparation of O-substituted oximes of ketones has already been described, in which alkali metal salts of ketoximes, or ketoximes in the presence of solid alkali metal hydroxides, are reacted with alkylating agents in dipolaraprotic solvents. For working up, water is added and the reaction product is extracted (compare EP-OS (European Published Specification) No. 0,023,560).

The solvents which are preferably used for this, such as N-methylpyrrolidone, dimethylacetamide, dimethyl sulphoxide, tetramethylene sulfone or hexamethylphosphoric acid triamide, are costly solvents, and some of them are toxicologically objectionable, and it is difficult to recover them because of their ready solubility in water and high boiling point. Thus, the value of this process is greatly restricted, especially with a view to industrial use.

Furthermore, it has been disclosed that O-substituted ketoximes and aldoximes can be obtained in an industrial process when oximes are reacted with an organic chloride and an alkali metal hydroxide in a low-molecular weight alcohol (compare EP-OS (European Published Specification) No. 0,121,701). However, the yields of the desired oxime ether are unsatisfactory. Thus, for example on methylation of benzaldoxime a mixture of 72.9% of O-methyl ether, 21.6% of nitrone and 4.7% of starting material are obtained (compare Example 1 of EP-OS (European Published Specification) No. 0,121,701).

None of the known processes is a suitable option for the preparation of 4-hydroxy-benzaldoxime O-ethers on an industrial scale.

The industrial process according to EP-OS (European Published Specification) No. 0,121,701, as well as all the other general alternatives listed, are also characterized in that, in particular, the alkylation of the oximes is carried out under basic conditions. This circumstance restricts the range of applicability of the process to those benzaldoximes which have no base-sensitive substituents on the aromatic ring and/or have no substituents to be attacked by the alkylating agent under basic conditions, such as, for example, phenolic OH groups.

It has now been found that known hydroxybenzaldoxime O-ethers of the formula

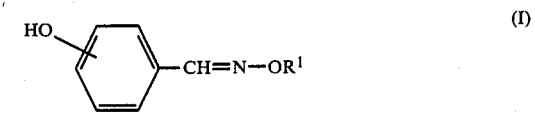

in which $R^1$ represents alkyl, alkenyl or alkynyl, are obtained when hydroxy-benzaldehydes of the formula

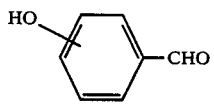

(II)

are reacted in the presence of an acid catalyst and, where appropriate, in the presence of a diluent, at temperatures between 50° C. and 150° C., with ketoxime O-ethers of the formula

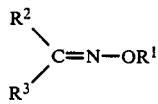

(III)

in which
R$^1$ has the abovementioned meaning, and
R$^2$ and R$^3$ are identical or different and represent an aliphatic, cycloaliphatic or aromatic radical, or
R$^2$ and R$^3$, together with the carbon atom to which they are bonded, represent cycloalkyl.

It may be designated as being extremely surprising that the reaction according to the invention takes place smoothly under the process conditions indicated. On the basis of the known state of the art it was to be expected that the desired reaction would take place only very slowly, since it is known that ketoxime ethers are very resistant to acids and bases. Thus, for example, hydrolysis only succeeds on prolonged heating with mineral acid (compare in this context, for example, Houben-Weyl, Methoden der Organischen Chemie, volume X/1, page 1186, Stuttgart 1981; Helv. Chim. Acta, vol. XLV, Fasc. 1 (1962) No. 40, page 359 and EP-OS (European Published Specification) No. 0,121,701).

Furthermore, it was to be expected that the ketone (R$^2$—CO—R$^3$) resulting on cleavage of the oxime ether would undergo extensive condensation, under acid catalysis, with the starting aldehyde of the formula (II), since it is known that hydroxy-benzaldehydes very readily react with ketones which contain a methylene group in the α-position to the carbonyl group, in an acid-catalyzed aldol condensation, to give α,β-unsaturated ketones (compare in this context Houben-Weyl, Methoden der Organischen Chemie, volume VII/2b, page 1457, Stuttgart 1976).

Finally, it was to be expected that the reaction according to the invention would stop at an unfavorable equilibrium mixture if the resulting ketone is not substantially removed from the reaction mixture. This is because it is known that oximes of non-volatile ketones can be obtained by transoximation with oximes of volatile ketones or aldehydes, it being necessary, however, always to remove the resulting volatile carbonyl compound by distillation (compare British Patent Specification No. 870,787).

In the case of the oximes, the removal of the resulting ketone by distillation is industrially straightforward because of the great differences in boiling points between the ketone or aldehyde and the relevant oxime.

However, the separation of ketone and relevant oxime ether in the process according to the invention is, because the differences in the boiling points are low in general, only possible by precision distillation which is time- and energy-consuming.

It is not possible in this way rapidly to remove the ketone R$^2$—CO—R$^3$ resulting in the reaction. For this reason, it would have been expected that further reaction of the ketone with excess hydroxy-benzaldehyde to give α, β-unsaturated ketones would take place to a large extent.

The process according to the invention is distinguished by a number of advantages. Thus, it makes it possible to prepare hydroxy-benzaldoxime O-ethers of the formula (I) in high yields, use being made of reasonably priced and readily available compounds as starting materials. Furthermore, the reaction is straightforward to carry out, and the isolation of the benzaldoxime O-ethers of the formula (I) involves no difficulty whatever. Hence the process according to the invention is especially suitable for the preparation of hydroxy-benzaldoxime O-ethers of the formula (I) on an industrial scale.

If, for example, 4-hydroxy-benzaldehyde and methyl isobutyl ketoxime O-methyl ether are used as starting materials, and concentrated sulphuric acid is used as the catalyst, then the course of the process according to the invention can be illustrated by the equation below:

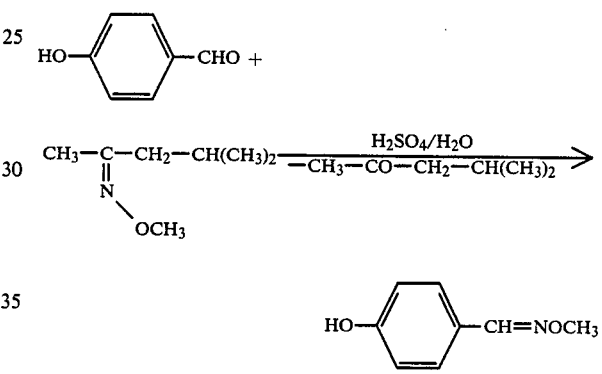

The hydroxy-benzaldehydes which are to be used as starting materials in the process according to the invention are generally defined by formula (II). 4-hydroxybenzaldehyde is particularly preferred.

The hydroxybenzaldehydes of the formula (II) are generally known compounds of organic chemistry (compare, for example, Houben-Weyl, Methoden der Organischen Chemie, volume VII, part 1 and E 3 (1983)).

The ketoxime O-ethers which are also to be used as starting materials for the process according to the invention are generally defined by formula (III). In this formula,
R$^1$ preferably represents straight-chain or branched alkyl having 1 to 10 carbon atoms, and represents straight-chain or branched alkenyl and alkynyl, each having 3 to 10 carbon atoms;
R$^2$ preferably represents straight-chain or branched alkyl having 1 to 10 carbon atoms, cycloalkyl having 5 to 7 carbon atoms, and represents phenyl which is optionally substituted once or twice, identically or differently, preferred substituents which may be mentioned being halogen and alkyl having 1 or 2 carbon atoms;
R$^3$ preferably represents straight-chain or branched alkyl having 1 to 10 carbon atoms, cycloalkyl having 5 to 7 carbon atoms, and represents phenyl which is optionally substituted once or twice, identically or differently, preferred substituents which may be mentioned being halogen and alkyl having 1 or 2 carbon atoms; and $R^2$ and $R^3$, together with the carbon atom to which they are bonded, preferably represent cycloalkyl having 5 to 7 carbon atoms.

Particularly preferred starting materials are those ketoxime O-ethers of the formula (III) in which $R^1$ represents straight-chain or branched alkyl having 1 to 4 carbon atoms;

$R^2$ represents straight-chain or branched alkyl having 1 to 6 carbon atoms, and represents phenyl;

$R^3$ represents straight-chain or branched alkyl having 1 to 6 carbon atoms, and represents phenyl; or $R^2$ and $R^3$, together with the carbon atom to which they are bonded, represent cyclohexyl or cycloheptyl.

The ketoxime O-ethers of the formula (III) are known or can be obtained in a known manner by reaction of ketoximes of the formula

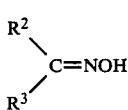 (IV)

in which $R^2$ and $R^3$ have the abovementioned meaning, with an alkylating agent, such as, for example, alkyl halides or dimethyl sulphate, in the presence of an inert organic solvent, such as, for example, methylene chloride, and in the presence of a base such as, for example, sodium hydroxide solution, and in the presence of a phase-transfer catalyst such as, for example, tetrabutylammonium bromide (compare in this context, for example, EP-OS (European Published Specification) No. 0,023,560, EP-OS (European Published Specification) No. 0,121,701 and the preparation examples). Those compounds of the formula (III) in which $R^1$ represents alkenyl or alkynyl can be prepared in an analogous manner.

The ketoximes of the formula (IV) are generally known compounds of organic chemistry. They can be prepared by reaction of ketones of the formula

 (V)

in which $R^2$ and $R^3$ have the abovementioned meaning, with with hydroxylamine or its salts, by customary methods, where appropriate in the presence of an inert organic diluent.

These oximes of the formula (IV) can be prepared in a particularly advantageous manner when a technical hydroxylamine salt solution is reacted with the ketone of the formula (V), where appropriate in the presence of an inert solvent which is sparingly soluble in water, such as, for example, cyclohexane, petroleum ether, toluene or benzene, in a pH range from 3 to 7, preferably from 5 to 6. For the working up, the organic phase is separated off and fractionally distilled. This results, after a forerun of excess ketone, in high yields of the oximes of the formula (IV) (compare also the preparation examples).

The ketones of the formula (V) are generally known compounds of organic chemistry. The following may be mentioned as examples:

Acetone, methyl isopropyl ketone, methyl n-propyl ketone, methyl isobutyl ketone, methyl ethyl ketone, tert.-butyl methyl ketone, di-n-propyl ketone, di-isopropyl ketone, di-isobutyl ketone, diethyl ketone, 5-methyl-3-heptanone, acetophenone, cyclohexanone and cycloheptanone.

The process according to the invention is, where appropriate, carried out in the presence of an organic solvent which is inert under the reaction conditions. This includes, preferably, alcohols such as methanol, ethanol, n-propanol, i-propanol, n-butanol or tert.-butanol; aliphatic and aromatic hydrocarbons such as petroleum ether, cyclohexane, benzene or toluene; ethers such as diisopropyl ether, tetrahydrofuran or dioxane, and halogenated hydrocarbons such as 1,2-dichloroethane.

Lewis acids are suitable and preferred catalysts for the process according to the invention. These include, preferably, acid salts of organic and inorganic acids. Examples which may be mentioned are: hydrochloric acid, sulphuric acid, phosphoric acid, benzenesulphonic acid, toluenesulphonic acid, alkylcarboxylic acids, alkylsulphonic acids, trifluoroacetic acid and fluorinated alkylsulphonic acids.

The reaction temperatures for carrying out the process according to the invention can be varied within a relatively wide range. In general, it is carried out at temperatures between 50° and 150° C. preferably between 50° and 100° C.

When carrying out the process according to the invention, in general 1 to 10 mols, is preferably 1 to 4 mols, of ketoxime O-ether of the formula (III) and 0.01 to 10 mol-% of catalyst relative to the ketoxime O-ether used are used for 1 mol of hydroxy-benzaldehyde of the formula (II).

An excess of ketoxime O-ether is not uneconomic because unreacted ketoxime O-ether can be removed from the reaction mixture by distillation and recycled.

To work up the reaction mixture, water is added, and the organic phase is separated off and fractionally distilled. However, every other alternative working-up is possible. For example, it may prove to be advantageous to remove the ketone, which is being formed, from the reaction mixture by fractional distillation.

The hydroxy-benzaldoxime O-ethers of the formula (I) which can prepared by the process according to the invention are generally valuable starting materials for the synthesis of biologically active compounds such as, for, example, the synthesis of oxime ethers which have good insecticidal properties (compare EP-OS (European Published Specification) No. 0,115,828); of azolylphenoxy derivatives which have outstanding fungicidal properties (compare EP-OS (European Published Specification) No. 0,076,370);of 1-hydroxyethyl-triazolyl derivatives which have good fungicidal and antimycotic properties (compare EP-OS (European Published Specification) No. 0,110,048 and DE-OS (German Published Specification) No. 3,314,548); and of hydroxyalkylazole derivatives which have good antimycotic activity (compare DE-OS (German Published Specification) No. 3,427,844).

Thus, for example, it is possible to prepare 3,3-dimethyl-1-(4-methoxyiminomethyl-phenoxy)-1-(1,2,4-triazol-1-yl)-2-butanone of the formula

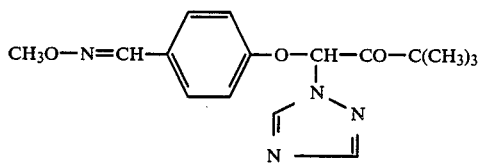

by first reacting 3,3-dimethyl-1-(1,2,4-triazol-1-yl)-2-butanone with bromine to give 1-bromo-1-(1,2,4-triazol-1-yl)-3,3-dimethyl-2-butanone, and then reacting the latter with 4-hydroxybenzaldoxime O-methyl ether in the presence of a base. This synthesis can be illustrated by formulae as follows:

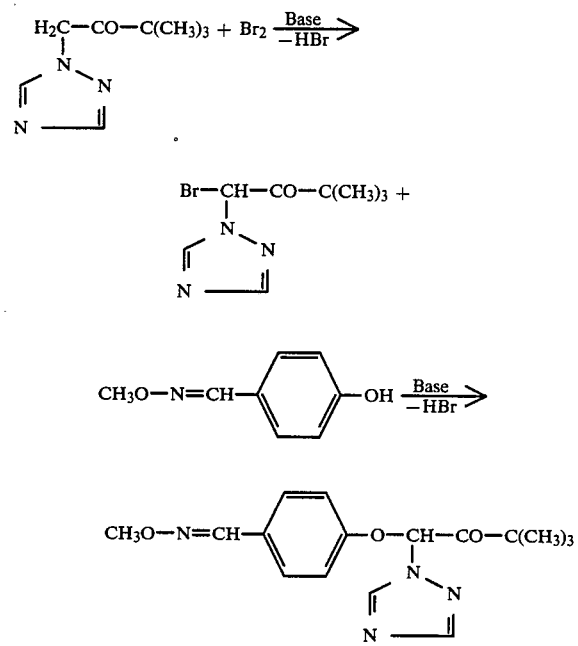

The process according to the invention is illustrated by the examples which follow.

EXAMPLE 1

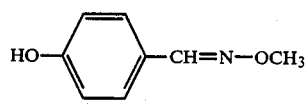

(I-1)

122 g (1 mol) of 4-hydroxybenzaldehyde, 258 g (2 mols) of methyl isobutyl ketoxime O-methyl ether and 9.8 g (0.05 mol) of 50% by weight sulphuric acid are stirred at 100° C. for 6 hours. The mixture is then allowed to cool, and is washed with water to neutrality, and the organic phase is distilled in vacuo.

After a fore-run of methyl isobutyl ketone and methyl isobutyl ketoxime O-methyl ether, 140.5 g (93% of theory) of 4-hydroxy-benzaldoxime O-methyl ether of boiling point 138°–142° C./0.1 Torr are obtained.

PREPARATION OF THE STARTING MATERIAL

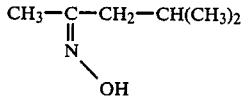 (III-1)

120 g (1.04 mols) of methyl isobutyl ketoxime, 500 g (2.5 mol) of 20% by weight sodium hydroxide solution and 33 g (0.104 mol) of tetrabutylammonium bromide are initially introduced into 500 ml of methylene chloride. At 40° C., 138 g (1.09 mols) of dimethyl sulphate are added dropwise, and the reaction mixture is then stirred at 40° C. for 7 hours. It is then cooled, and the organic phase is separated off, washed with water, dried over sodium sulphate and fractionally distilled. 84 g (60% of theory) of methyl isobutyl ketoxime O-methyl ether bdiling over the range 120°–129° C. 760 Torr are obtained.

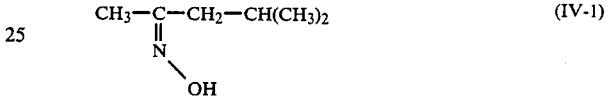 (IV-1)

2950 g (5 moles) of 14% by weight technical hydroxylamine sulphate solution is adjusted to a pH of 5 to 6 using half-concentrated sodium hydroxide solution. At 20°–30° C., 1,000 g (10 mols) of methyl isobutyl ketone are added, and the pH is maintained constant during the course of the reaction by further addition of sodium hydroxide solution. The reaction is complete after 2 hours. The organic phase is separated off, washed with water, dried over sodium sulphate and distilled. 515 g (89.6% of theory based on hydroxylamine used) of methyl isobutyl ketoxime of boiling point 88°–91° C./35 Torr are obtained.

PREPARATION OF OTHER STARTING MATERIALS OF THE FORMULA (III)

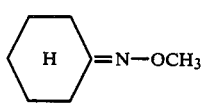 (III-2)

113 g (1 mol) of cyclohexanone oxime, 213 g (2.4 mols) of 45% by weight sodium hydroxide solution and 32 g (0.1 mol) of tetrabutylammonium bromide are initially introduced into 500 ml of methylene chloride. At 40° C., 139 g (1.1 mols) of dimethyl sulphate are added drop-wise, and the mixture is then stirred at 40° C. for 7 hours. Then water is added. The organic phase is separated off, dried over sodium sulphate and fractionally distilled.

70 g (55% of theory) of cyclohexanone oxime O-methyl ether boiling over the range 160°–164° C./760 Torr are obtained.

It will be understood that the specification and examples are illustrative but not limitative of the present invention and that other embodiments within the spirit and scope of the invention will suggest themselves to those skilled in the art.

I claim:

1. A process for the preparation of a hydroxybenzaldoxime O-ether of the formula

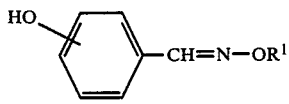

in which
R$^1$ is alkyl, alkenyl or alkynyl
comprising reacting a hydroxybenzaldehyde of the formula

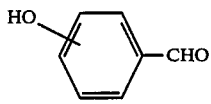

in the presence of an acid catalyst at a temperature between 50° to 150° C. with a ketoxime O-ether of the formula

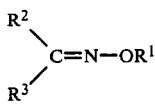

in which
R$^2$ and R$^3$ each independently is an aliphatic cycloaliphatic or aromatic radical, or
R$^2$ and R$^3$, together with the carbon atom to which they are bonded are cycloalkyl.

2. A process according to claim 1, wherein the hydroxybenzaldehyde is 4-hydroxybenzaldehyde.

3. A process according to claim 1, in which
R$^1$ is alkyl having 1 to 20 carbon atoms, or alkenyl or alkynyl, each having 3 to 10 carbon atoms,
R$^2$ and R$^3$ each independently is alkyl having 1 to 10 carbon atoms, cycloalkyl having 5 to 7 carbon atoms, or phenyl which is optionally substituted once or independently twice by halogen and/or alkyl having 1 or 2 carbon atoms, or
R$^2$ and R$^3$, together with the carbon atom to which they are bonded, are cycloalkyl having 5 to 7 carbon atoms.

4. A process according to claim 1, wherein the acid catalyst is a Lewis acid.

5. A process according to claim 1, wherein the reaction is carried out at a temperature between 50° and 100° C.

6. A process according to claim 1, wherein 1 to 10 mols of the ketoxime O-ether are present per mol of hydroxybenzaldehyde and the catalyst is present in 0.01 to 10 mol % based on the ketoxime O-ether.

7. A process according to claim 1, wherein the reaction is effected in a diluent.

8. A process according to claim 3, wherein the hydroxybenzaldehyde is 4-hydroxybenzaldehyde, the acid catalyst is a Lewis acid, the reaction is effected in a diluent at a temperature between 50° and 100° C., 1 to 10 mols of the ketoxime O-ether are present per mol of hydroxybenzaldehyde and the catalyst is present in 0.01 to 10 mol % based on the ketoxime O-ether.

9. A process according to claim 1, wherein at the end of the reaction the hydroxybenzaldoxime is separated from the by-product ketone corresponding to the starting ketoxime O-ether.

* * * * *